(12) United States Patent
Shoemaker Ellis (10) Patent No.: US 9,891,170 B1
(45) Date of Patent: Feb. 13, 2018

(54) STAND ALONE PORTABLE SENSING SYSTEM FOR ADVANCED NANOPARTICLE TRACERS

(71) Applicant: Saudi Arabian Oil Company, Dhahran (SA)

(72) Inventor: Erika Shoemaker Ellis, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/450,979

(22) Filed: Mar. 6, 2017

(51) Int. Cl.
| | |
|---|---|
| G01N 21/64 | (2006.01) |
| G01N 33/28 | (2006.01) |
| E21B 49/08 | (2006.01) |
| E21B 43/34 | (2006.01) |
| E21B 47/10 | (2012.01) |
| C02F 1/38 | (2006.01) |
| B01D 24/00 | (2006.01) |
| C02F 101/32 | (2006.01) |
| C02F 103/10 | (2006.01) |

(52) U.S. Cl.
CPC .......... *G01N 21/643* (2013.01); *B01D 24/00* (2013.01); *C02F 1/38* (2013.01); *E21B 43/34* (2013.01); *E21B 47/1015* (2013.01); *E21B 49/086* (2013.01); *E21B 49/088* (2013.01); *G01N 33/2823* (2013.01); *C02F 2101/32* (2013.01); *C02F 2103/10* (2013.01); *G01N 2021/6439* (2013.01)

(58) Field of Classification Search
USPC ......................................... 250/288, 281, 282
See application file for complete search history.

(56) References Cited

U.S. PATENT DOCUMENTS

| | | | |
|---|---|---|---|
| 5,110,471 A | 5/1992 | Kalnins | |
| 6,355,416 B1 * | 3/2002 | Abramson | ............... C12Q 1/68 435/6.12 |
| 8,596,354 B2 | 12/2013 | Hartshorne et al. | |
| 9,108,142 B2 | 8/2015 | England | |
| 2008/0105032 A1 * | 5/2008 | Reddy | ..................... E21B 49/08 73/23.41 |
| 2014/0260694 A1 | 9/2014 | Szlendak | |
| 2015/0130468 A1 | 5/2015 | Christian et al. | |
| 2015/0361791 A1 * | 12/2015 | Gisolf | ..................... E21B 49/00 250/356.2 |
| 2015/0377021 A1 | 12/2015 | El-Khazindar et al. | |

* cited by examiner

*Primary Examiner* — Kiet T Nguyen
(74) *Attorney, Agent, or Firm* — Bracewell LLP; Constance G. Rhebergen; Brian H. Tompkins (57) ABSTRACT

A portable sensing system for nanomaterial tracers used in oil producing wells is provided. The portable sending system includes a separation device such as a hydrocyclone or carboy, a filtration device having filtration media, a waste container, and spectrometer. The portable sensing system may also include or be connected to a portable computer such as a laptop. The portable sensing system may be connected to a wellhead without any modification of the wellhead or a producing line. Additionally, the portable sensing system may perform separation, filtration, and detection on a sample without manual or automatic pumps and other moving parts, and using gravity and the existing fluid pressure of the sample to promote fluid flow for the separation, filtration, and detection.

18 Claims, 5 Drawing Sheets

STAND ALONE PORTABLE SENSING SYSTEM FOR ADVANCED NANOPARTICLE TRACERS

BACKGROUND

Field of the Disclosure

The present disclosure generally relates to the analysis of hydrocarbon reservoirs. More specifically, embodiments of the disclosure relate to the detection of fluorescent tracers introduced into such reservoirs.

Description of the Related Art

Crude oil is the world's main source of hydrocarbons that are used as fuel and petrochemical feedstock. One overriding problem in exploring for hydrocarbons in the subsurface is related to the probing and characterization of an environment that cannot be seen. After a hydrocarbon deposit has been discovered and is ready to be developed and exploited, many assumptions must be made by reservoir geologists and reservoir engineers in the modeling of a large volume of rock which cannot be seen. For example, it may be desirable to map high permeability pathways in a reservoir.

In some instances, chemical tracers (for example, radioactive chemical tracers) may be introduced with injection fluids. However, the large amounts of chemical tracers used may be expensive. Additionally, the use of chemical tracers requires collection and transportation to a laboratory for analysis; the collection and lab processing may also add additional cost to the use of chemical tracers.

Nanomaterial (for example, nanoparticle) tracers may provide an effective and less expensive alternative to chemical tracers. For example, fluorescent nanoparticle tracers may be used in a manner similar to chemical tracers. However, the use of the nanomaterial tracers may still require collection and transportation to a laboratory for analysis, both of which add cost and time to the analysis of reservoir and associated formation.

SUMMARY

Fluorescent nanomaterial tracers may be used in reservoir analysis to enhance reservoir oil recovery in secondary produced wells. Carbon-based fluorescent nanoparticle tracers (which may include or be referred to as "A-Dots") or other functionalized fluorescent nanoparticle or nanotechnology-based tracers referred to as "nanomaterial tracers" or "nanomaterial tracer agents" may have sufficient long-term stability in high temperature and high salinity environments to survive transit through the subsurface between wells. Such tracers may be introduced into the reservoir through an injector well to subsequently flow through the reservoir. The tracers may not only trace flow paths between wells but may also be used to obtain information about the reservoir through which they pass and transfer the information in the form of a change of fluorescence of the nanomaterial. The tracers may then be recovered back at the surface from a producing well for sampling, detection, and testing. For example, carbon-based nanoparticles may fluoresce at a specific wavelength; thus, fluorescence spectrometry can be used to fingerprint the nanoparticles as they arrive at the producing well.

Typically, sample collection is done manually by traveling to a site periodically and collecting samples from the wells at each site. The purification of samples to prepare for fluorescence detection may be very time-consuming. For example, multiple dichloromethane (DCM) extractions may require about 30 hours of laboratory time for each sample collected in each period.

In one embodiment, a portable system for detecting nanomaterial tracers in fluid produced from a well. The portable system includes a separation device connectable to a wellhead without modification of the wellhead. The separation device is configured to receive a sample of production fluid from the wellhead and separate crude oil and water in the sample. The separation device includes a hydrocyclone or a carboy operable without electric power. The portable system further includes a filtration device connected to the separation device and including filtration media. The separation device is operable without electric power to filter a separated fluid received from the separation device. The portable system also includes a spectrometer connected to the filtration device and operable to receive a filtered fluid from the filtration device and measure a spectrum of the filtered fluid.

In some embodiments, the portable system includes a portable computer coupled to the spectrometer via a wired connection, and, in some embodiments, the spectrometer is operable to receive power solely from the portable computer via the wired connection. In some embodiments, the portable system includes a waste container arranged to receive crude oil from the filtration device. In some embodiments, the waste container is further arranged to receive the filtered fluid from the spectrometer after measurement of the spectrum. In some embodiments, the filtration media includes a clay that includes zeolite. In some embodiments, the spectrometer includes a light-emitting diode (LED) or laser diode array arranged to emit light into a test cell, such that the test cell configured to contain the filtered fluid. In some embodiments, the sample includes a nanomaterial tracer, such that the spectrum indicates fluorescence emitted by the nanomaterial tracer at a wavelength. In some embodiments, the portable system does not include a pump.

In another embodiment, a method for detecting nanomaterial tracers in fluid produced from a well is provided that includes receiving a sample of a production fluid from a wellhead in a separation device configured to separate crude oil and water in the sample. The separation device includes a hydrocyclone or a carboy operable without electric power, and the separation device is connected to the wellhead without modification of the wellhead. The method also includes separating, by the separation device, the crude oil and the water in the sample and filtering, by a filtration device connected to the separation device, the separated water. The filtration device includes filtration media. The method further includes measuring, via a spectrometer connected to the filtration device, a spectrum of the filtered water.

In some embodiments, the method includes transmitting the measurements over a wired connection from the spectrometer to a portable computer. In some embodiments, the spectrometer is operable to receive power solely from the portable computer via the wired connection. In some embodiments, the method includes disposing the separated crude oil in a waste container connected to the separation device. In some embodiments, the filtration media includes a clay that includes zeolite. In some embodiments, the spectrometer includes a light-emitting diode (LED) or laser diode array arranged to emit light into a test cell, such that the test cell is configured to contain the filtered fluid. In some embodiments, the sample includes a nanomaterial tracer, such that the spectrum indicates fluorescence emitted by the nanomaterial tracer at a wavelength.

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Fluorescent nanomaterial tracers, such as nanoparticle tracers, may be used for in-situ sensing and intervention in target reservoirs. Such nanomaterial tracers have sufficient long term stability in both high temperature and high salinity environments, allowing the tracers to survive transit through the subsurface between wells. The nanomaterial tracers can be introduced into the reservoir through an injector well, where they flow through the reservoir. The nanomaterial tracers may then be sampled and detected when the nanomaterials are recovered back at the surface from a producing well. A used herein, the term "nanomaterials" includes but is not limited to nanoparticles.

Embodiments of the disclosure include a portable sensing system for real-time detection of fluorescent nanomaterial tracers. The portable sensing system may be connected to a spigot on a sample line or producing line of a wellhead coupled to a well drilled to access a hydrocarbon reservoir in a formation. In some embodiments, the portable sensing system includes a hydrocyclone, a waste drum, a filtration device, a spectrometer, and a portable computer. In some embodiments, the portable sensing system may include two or more hydrocyclones. In some embodiments, the portable sensing system includes a carboy, a waste drum, a filtration device, a spectrometer, and a portable computer.

Advantageously, the portable sensing system may perform sampling and detection without any modification of the wellhead and producing line. As discussed in the disclosure, the portable sensing system is connected to an existing wellhead spigot and any obtained samples are not reintroduced to a producing line. Further, in some embodiments, the portable sensing system does not include any pumps or other moving parts and only uses the fluid pressure of a sample and gravity for separation, filtration, and flow through a spectrometer. The portable sensing system may have reduced power requirements as compared to existing sampling and sensing systems. For example, embodiments of the portable sensing system described herein may not include a pump, an automatic sampler, high pressure operations or devices, or any combination thereof, thus reducing power requirements as compared to existing systems. Additionally, the entire portable sensing system is portable and may enable analysis to be performed in the field without the transmission of data to a remote computer. The portable sensing system also provides for cost-effective and routine sample collection and detection.

Example nanoparticle tracers for use with the embodiments described herein may include carbon-based nanoparticles (which may include or be referred to as A-Dots) having functional groups that can be excited at a wavelength between about 400 nm and 500 nm. Fluorescence quantum yield (i.e., photons emitted/photons absorbed) can be about 10%, and is generally independent of the excitation wavelength, which, in some embodiments, may be in the range of about 400 to about 500 nm. In some embodiments, emission may be monitored at a wavelength of about 440 nm, although in other embodiments emission may be monitored at other wavelengths as well. In some embodiments, upon excitation, an example nanoparticle tracer may emit fluorescence that may be detected at a wavelength of about 440 nm to about 475 nm. It should be appreciated that, in other embodiments, other nanomaterial tracers having fluorescence capability may be sensed using the portable sensing system described in the disclosure.

Figure 1:
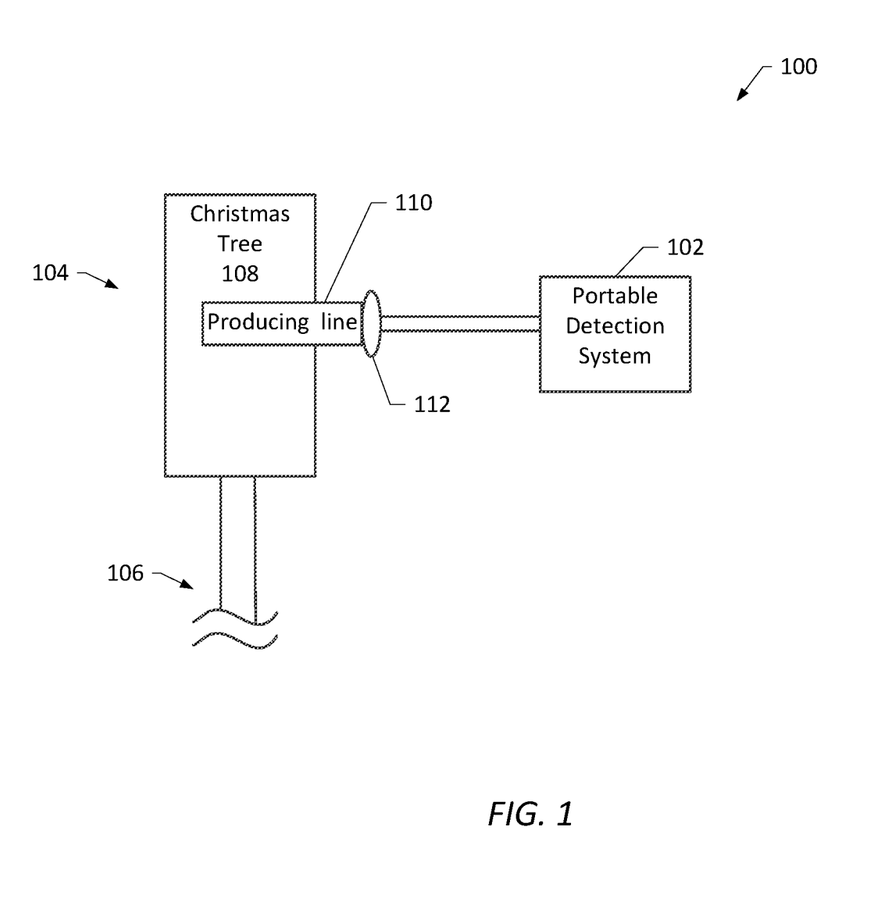
FIG. 1 is a block diagram of a hydrocarbon production environment and a portable sensing system connected to a wellhead in accordance with an embodiment of the disclosure.

FIG. 1 is a block diagram of a hydrocarbon production environment 100 illustrating a portable sensing system 102 connected to a wellhead 104 in accordance with an embodiment of the disclosure. As will be appreciated, the wellhead 104 may be coupled to a hydrocarbon reservoir via a well 106 that enables production of hydrocarbons from the reservoir. The well 106 may be a producing well analyzed via the introduction of one or more fluorescent nanomaterial tracers. For example, the one or more fluorescent nanomaterial tracers may be injected in an injector well in fluid connection with the producing well 106, such that the nanomaterial tracers may exit the well 106 via the wellhead 104.

The wellhead 104 may include multiple components that control and regulate activities and conditions associated with the well 106. For example, the wellhead 104 generally includes bodies, valves and seals that route produced hydrocarbons from via the well 106. In the illustrated embodiment, the wellhead 104 may include or be coupled to an assembly of valves, spools, and fittings referred to as a Christmas tree 108. The Christmas tree 108 may include a variety of flow paths (for example, bores) and may also include valves, fittings, and controls for operating the well 106. Accordingly, produced hydrocarbons (for example, oil) flow from the well 106 via the Christmas tree 108 before being routed to shipping or storage facilities.

The portable sensing system 102 may carried in a portable case to the site of the well 106. Advantageously, as described herein, the portable sensing system 102 may omit any batteries, pumps, or other electrically powered components to facilitate portability, usability, and transportation to the well site. As shown in FIG. 1, the portable sensing system 102 may be connected to a line 110 (for example, a line transporting production fluid, such as a producing line or a sample line) of the wellhead 104 via a spigot 112. For example, the line 110 may provide samples from a producing line that carries produced fluid from the well 106 via the wellhead 104. As described further below, the portable sensing system 102 may receive a sample of production fluid via the line 110 by the opening of the spigot 112. For example, in some embodiments, the spigot 112 may be periodically and manually opened by an operated to obtain a sample from the line 110. As described below, the portable sensing system 110 may separate, filter, and analyze fluid from the sample to detect the presence of nanomaterial tracers used for characterizing the well 106.

Figure 2:
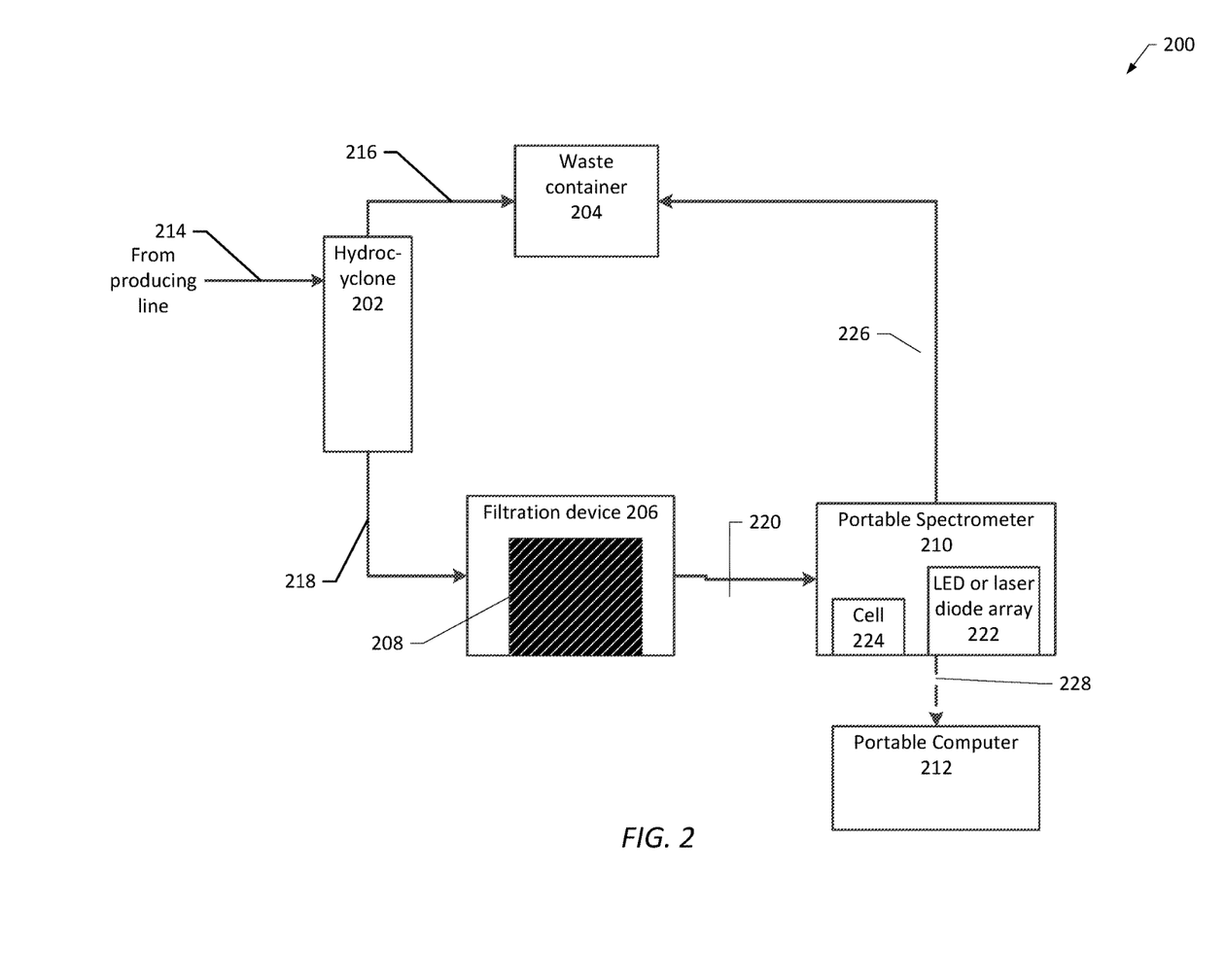
FIG. 2 is a block diagram of the components of a portable sensing system in accordance with an embodiment of the disclosure.

FIG. 2 depicts a portable sensing system 200 and its various components in accordance with an embodiment of the disclosure. As shown in FIG. 2, the portable sensing system 200 may include one or more hydrocyclones 202, a waste container 204, a filtration device 206 having filtration media 208 and a portable spectrometer 210. In some embodiments, the system 200 may include or be connected to a portable computer 212. As described below, in some embodiments, the portable sensing system 200 does not include any pumps, automatic samplers, or other moving parts and only uses the pressure of the sample and gravity for separation, filtration, and flow through a spectrometer.

In some embodiments, components of the portable sensing system 200 may be contained in a case, a housing, or other enclosure to facilitate portability and transportation to a well site. For example, in some embodiments, the one or more hydrocyclones 202, the waste container 204, the filtration device 206 and a portable spectrometer 210 may be contained in a portable case and transported to a well site. In some embodiments, the one or more hydrocyclones 202, the waste container 204, the filtration device 206 and a portable spectrometer 210 may be removed from the case and then connected and used in the manner described herein and as illustrated in FIG. 2. In some embodiments, the portable computer 212 may also be contained in a case or other enclosure.

The hydrocyclone 202 may include a connector to enable connection to a spigot of a wellhead, as shown by line 214 and as discussed above with regard to FIG. 1. Thus, the portable sensing system 200 may be connected to a wellhead without any modification of the wellhead or producing line. For example, a connector of the hydrocyclone 202 may be connected to a wellhead spigot via a hose, pipe, or other tubing. In some embodiments, the system 200 may include a pressure gauge and a choke disposed between the hydrocyclone 202 and the wellhead to reduce the pressure in the sample obtained from the wellhead.

The hydrocyclone 202 may separate oil and water from the sample collected from the wellhead. In some embodiments, the hydrocyclones may be compact or miniature hydrocyclones (also referred to as "mini-cyclones") and have approximately the same size as a one liter bottle. As will be appreciated, the hydrocyclone 202 may separate oil from water using gravity and the difference in density between oil and water, and without any moving parts. The lower density fluid (for example, oil) exits the top of the hydrocyclone (as shown by line 216) and the high density fluid (for example, water) exits the bottom of the hydrocyclone (as shown by line 218). Thus, in some embodiments, the hydrocyclone 202 may perform separation of the sampled fluid without manual or automatic pumps, electric power, or other similar requirements. In some embodiments, the portable sensing system 200 may include two hydrocyclones arranged in series and connected to the wellhead as described herein. In some embodiments, the hydrocyclone 202 may be a miniature hydrocyclone manufactured by Chemindustrial Systems, Inc. of Cedarburg, Wis., USA.

As shown in by line 216 in FIG. 2, the oil separated from the sample in the hydrocyclone 202 may be directed to the waste container 204 (for example, a drum). For example, a connector at the top of the hydrocyclone 202 may be connected to the waste container 204 via a hose, pipe, or other suitable tubing. The size of the waste container 204 may be selected to ensure sufficient volume for the collection of separated oil and other fluids disposed of by the portable sensing system 200 yet remain of a size suitable for maintaining the portability of the portable sensing system 200. For example, in some embodiments, the waste container 204 may be sized to enable period collection of samples over a time period, such as multiple days, multiple weeks, or greater time periods.

As also shown in FIG. 2, the water separated from the sample in the hydrocyclone 202 may be directed to the filtration device 206 having the filtration media 208. For example, a connector at the bottom of the hydrocyclone 202 may be connected to the filtration device 206 via a hose, pipe, or other suitable tubing. The filtration device 206 may separate contaminants such as organic compounds, metals, and emulsions that may interfere with detection of the fluorescent nanomaterial tracers from the separated water. In some embodiments, the filtration device 206 may perform filtration of the separated water from the hydrocyclone 202 without manual or automatic pumps, electric power, or other similar requirements.

The filtration device may include the filtration media 208. The filtration media 208 may a media that does not modify the signature of the nanomaterial tracers and that does not become consumed too quickly in order to extend the service life of the filtration device 204 and the portable sensing system 200. In some embodiments the filtration device 206 may be a drum that contains the filtration media 208. For example, on some embodiments, the filtration device 206 may be a 5 gallon drum containing about 5 gallons of filtration media 208.

In some embodiments, the filtration media 208 may be a granular filtration media and may be a zeolite-based clay (that is, a clay that includes zeolite). In some embodiments, the filtration media may be Hydrosil manufactured by Hydrosil International LTD. of East Dundee, Ill., USA. In such embodiments, for a sample size of about 500 ml having a 5% oil cut, a 5 gallon amount of filtration media may have a life of 700 samples or, in some embodiments, 170 weeks of sampling at a rate of 4 samples per week.

As shown by line 220 in FIG. 2, the filtered water from the filtration device 206 may be provided to the portable spectrometer 210. For example, a connector of the filtration device may be connected to the spectrometer 210 via a hose, pipe, or other suitable tubing. In some embodiments, the spectrometer 210 may be powered solely by power received from the portable computer 212. In other embodiments, the spectrometer may be powered by a separate battery (for example, a battery in a housing of the spectrometer) or may be powered by a combination of a separate battery and power received from the portable computer 212.

The spectrometer 210 may include an LED or laser diode array 222 and a flow cell 224. The flow cell 224 may move the sample of filtered water through the spectrometer 210, and the LED 222 may emit light into the sample. The fluorescence emitted by the nanomaterial tracers may then be detected by a detector (for example, a charge-coupled device (CCD) array) of the spectrometer 210. In some embodiments, for example, the LED or laser diode array 222 may be a modular LED having dimensions of about 3 inches×3 inches×3 inches. In some embodiments, the spectrometer 210 may be an Ocean Optics USB2000 manufactured by Ocean Optics Inc, of Dunedin, Fla., USA. The spectrometer 210 may take measurements of a sample in the flow cell 224 at specific intervals. In some embodiments, the spectrometer 210 may detect the nanomaterial tracers at concentrations of at least parts-per-billions (ppb). In some embodiments, the spectrometer 210 may have a detection range of about 200 nm to about 1100 nm.

In some embodiments, as shown by line 226 in FIG. 2, the filtered water analyzed by the spectrometer 210 may be directed to the waste container 204. For example, an outlet of the portable spectrometer 210 (for example, an outlet connected to the flow cell 224) may be connected to a connector on the waste container 204 via a hose, pipe, or other tubing. The waste container 204 may be periodically emptied to an onsite or offsite disposal facility, such as at a regular time interval or when the waste container 204 contains a specific amount of fluid.

The measurements from the spectrometer 210 may be transmitted to the portable computer 212, such as over a wired connection 228. The portable computer 212 may store the measurements received from the spectrometer 210. In some embodiments, the portable computer 212 may provide a user interface for viewing the measurements, analyzing the measurements (for example, generating a plot of the measurements versus one or more parameters), and, in some embodiments, transmitting the measurements to another computer. For example, in some embodiments, the portable computer 212 may transmit the stored measurements over a wireless network (for example, a cellular network) to another computer.

In some embodiments, the portable computer 212 may be a laptop, a tablet, a smartphone, or other suitable portable computer 212. In some embodiments, the portable computer 212 may be a weather-resistant computer, such as a weather-resistant laptop. The portable computer 212 may include, for example, a processor, a memory, and a display. The processor (as used the disclosure, the term "processor" encompasses microprocessors) and may include one or more processors having the capability to receive and process data received from the spectrometer 210. The processor may also include a single-core processors and multicore processors and may include graphics processors.

The portable computer 212 may also include a memory (which may include one or more tangible non-transitory computer readable storage mediums) that may include volatile memory, such as random access memory (RAM), and non-volatile memory, such as ROM, flash memory, a hard drive, any other suitable optical, magnetic, or solid-state storage medium, or a combination thereof. The memory of the portable computer 212 may store executable computer code that may include, for example, executable computer code for processing data received from the spectrometer 210 and displaying data received from the spectrometer 210, such as on a display of the portable computer 212.

Accordingly, the portable computer 212 may also include a display, such as a liquid crystal display (LCD), an organic light emitting diode (OLED) display, or other suitable display. The display may display a user interface (for example, a graphical user interface) that may enable a user to obtain and view data from the spectrometer 210. In some embodiments, the portable computer 212 may include a touch screen display and may include or be provided with touch sensitive elements through which a user may interact with the user interface. In some embodiments, the portable computer 212 may display measurements obtained from the spectrometer 212, such as in a table or as a graph of measurements (for example, a graph of intensity vs. wavelength, as shown below in FIG. 3).

In some embodiments, the portable computer 212 may include a network interface that provides for communication between the portable computer 212 and other computers remote from the well site of the portable sensing system 200. Such a network interface may include a wired network interface card (NIC), a wireless (for example, radio frequency) network interface card, or combination thereof. In some embodiments, the portable computer 212 may provide for the transmission of measurement data obtained from the spectrometer 210 to another computer remote from the well site.

Figure 3:
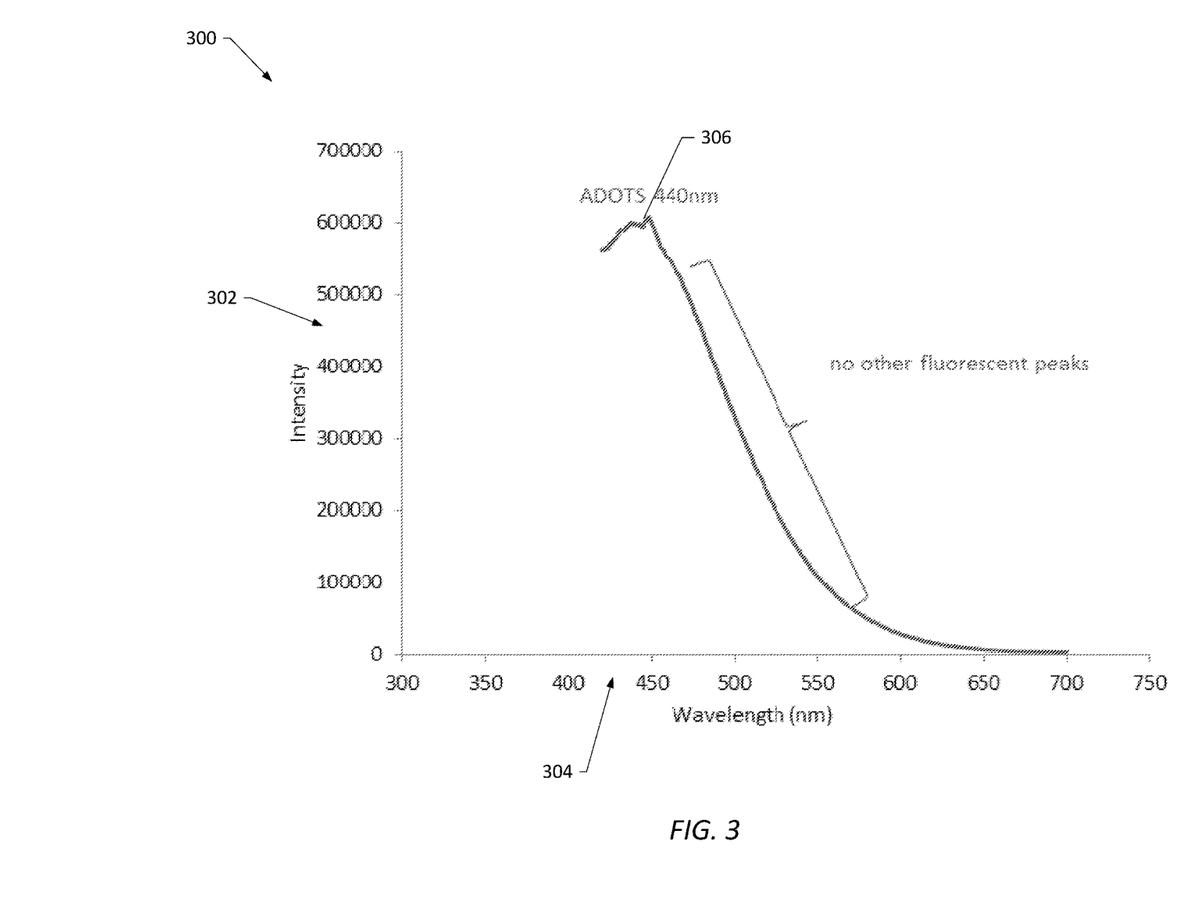
FIG. 3 is a plot of measurements obtained by an example portable sensing system having components as illustrated in FIG. 2 in accordance with an embodiment of the disclosure.

FIG. 3 depicts a plot 300 of measurements obtained by an example portable sensing system having components as described above and illustrated in FIG. 2. The samples were obtained from an example producing well. The measurements were generated from an embodiment of the portable sensing system 200 having two hydrocyclones in series and using Hydrosil as the filtration media. Accordingly, the plot shown in FIG. 3 depicts the measured fluorescence intensity (on the y-axis 302 and in counts-per-second)) vs. wavelength (shown in the x-axis 304 in seconds(s)).

As shown in FIG. 3, the nanoparticle tracers present in the measured samples exhibited an intensity peak 306 at about 440 nm. The intensity peak 440 nm of the nanoparticle tracers is clearly evident, and no other fluorescence peaks from other contaminants are present, thus illustrating the efficacy of the portable sensing systems described in the disclosure. That is, other contaminants potentially having fluorescence peaks that could interfere with detection of the nanoparticle tracers were sufficiently removed during the separation (for example, via the hydrocyclone 202) and filtration (for example, via the filtration device 206) described above.

Figure 4:
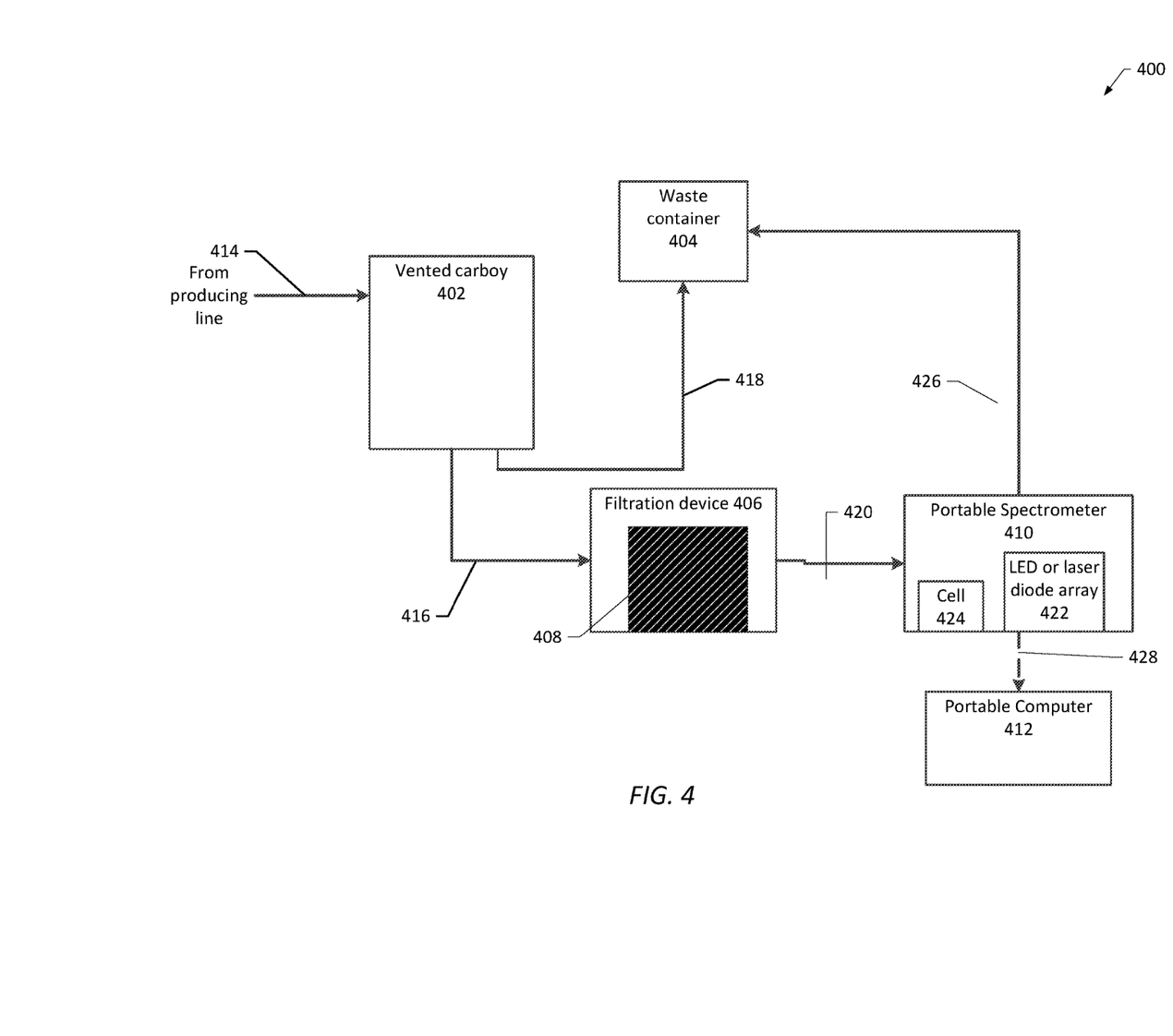
FIG. 4 is a block diagram of the components of a portable sensing system in accordance with an embodiment of the disclosure.

FIG. 4 depicts a portable sensing system 400 and its various components in accordance with another embodiment of the disclosure. As shown in FIG. 4, the portable sensing system 400 may include a vented carboy 402, a waste container 404, a filtration device 406 having filtration media 408, and a portable spectrometer 410. In some embodiments, the system 400 may include or be connected to a portable computer 412. As described below, in some embodiments, the portable sensing system 400 does not include any pumps or other moving parts and only uses the pressure of the sample and gravity for separation, filtration, and flow through a spectrometer.

In some embodiments, components of the portable sensing system 400 may be contained in a case, a housing, or other enclosure to facilitate portability and transportation to a well site. For example, in some embodiments, the vented carboy 402, the waste container 404, the filtration device 406 and a portable spectrometer 410 may be contained in a portable case and transported to a well site. In some embodiments, the vented carboy 402, the waste container 404, the filtration device 406 and a portable spectrometer 410 may be removed from the case and then connected and used in the manner described herein and as illustrated in FIG. 4. In some embodiments, the portable computer 412 may also be contained in a case or other enclosure.

The vented carboy 402 may include a connector to enable connection to a producing line (for example, via a spigot of a wellhead), as shown by line 414 and as discussed above with regard to FIG. 1. Thus, the portable sensing system 400 may be connected to a wellhead without any modification of the wellhead or producing line. For example, a connector of the hydrocyclone 202 may be connected to a wellhead spigot via a hose, pipe, or other tubing. In some embodiments, the system 400 may include a pressure gauge and a choke disposed between the vented carboy 402 and the wellhead to reduce the pressure in the sample obtained from the wellhead before the sample enters the vented carboy 402.

The vented carboy 402 may separate oil and water from the sample collected from the wellhead. As will be appreciated, the vented carboy 402 may separate oil from water using gravity and the difference in density between oil and water, and without any moving parts. The higher density fluid (for example, water) may settle to the bottom of the vented carboy 402 and may exit the bottom of the vented carboy 402 (as shown by line 416). Thus, in some embodiments, the vented carboy 402 may perform separation of the sampled fluid without manual or automatic pumps, electric power, or other similar requirements.

As shown in by line 418 in FIG. 4, the oil separated from the sample in the vented carboy 402 may be disposed in the waste container 404 (for example, a drum). For example, the separated oil in the carboy may be periodically disposed of in the waste container 404. The size of the waste container 404 may be selected to ensure sufficient volume for the collection of separated oil and other fluids disposed of by the portable sensing system 400 yet remain of a size suitable for maintaining the portability of the portable sensing system 400. For example, in some embodiments, the waste container 404 may be sized to enable period collection of samples over a time period, such as multiple days, multiple weeks, or greater time periods.

As also shown in FIG. 4, the water separated from the sample in the vented carboy 402 may be directed to the filtration device 406 having the filtration media 408. For example, a connector at the bottom of the vented carboy 402 may be connected to the filtration device 406 via a hose, pipe, or other suitable tubing. The filtration device 406 may operate in a manner similar to the filtration device 206 described above. In some embodiments, the filtration device 406 may perform filtration of the separated water from the vented carboy 402 without manual or automatic pumps, electric power, or other similar requirements.

The filtration device 406 may include the filtration media 408. In some embodiments the filtration device 406 may be a drum that contains the filtration media 408. For example, on some embodiments, the filtration device 406 may be a 5 gallon drum containing about 5 gallons of filtration media 408.

The filtration media 408 may be similar to the filtration media 208 described above. In some embodiments, the filtration media 408 may be a granular filtration media and may be a zeolite-based clay. In some embodiments, the filtration media may be Hydrosil manufactured by Hydrosil International LTD. of East Dundee, Ill., USA. In such embodiments, for a sample size of about 500 ml having a 5% oil cut, a 5 gallon amount of filtration media may have a life of 700 samples or, in some embodiments, 170 weeks of sampling at a rate of 4 samples per week.

As shown by line 420 in FIG. 4, the filtered water from the filtration device 406 may be provided to the portable spectrometer 410. For example, a connector of the filtration device 406 may be connected to the spectrometer 410 via a hose, pipe, or other suitable tubing. In some embodiments, the spectrometer 410 may be powered solely by power received from the portable computer 412. In other embodiments, the spectrometer may be powered by a separate battery (for example, a battery in a housing of the spectrometer) or may be powered by a combination of a separate battery and power received from the portable computer 412.

The spectrometer 410 may be similar to the spectrometer 210 described above and may include an LED or laser diode array 422 and a flow cell 424 that operate in a similar manner. In some embodiments, for example, the LED or laser diode array 422 may be a modular LED having dimensions of about 3 inches×3 inches×3 inches. In some embodiments, the spectrometer 410 may be an Ocean Optics USB2000 manufactured by Ocean Optics Inc, of Dunedin, Fla., USA. The spectrometer 410 may take measurements of a sample in the flow cell 424 at specific intervals. In some embodiments, the spectrometer 410 may detect the nanomaterial tracers at concentrations of at least parts-per-billions (ppb). In some embodiments, as shown by line 426 in FIG. 4, the filtered water analyzed by the spectrometer 410 may be directed to the waste container 404. For example, an outlet of the portable spectrometer 410 (for example, an outlet connected to the flow cell 424) may be connected to a connector on the waste container 404 via a hose, pipe, or other tubing.

The measurements from the spectrometer 410 may be transmitted to the portable computer 412, such as over a wired connection 428. The portable computer 412 may store the measurements received from the spectrometer 410. Here again, in some embodiments, the portable computer 412 may be a laptop, a water-resistant laptop, a tablet, a smartphone, or other suitable portable computer 412. In some embodiments, the portable computer 412 may provide a user interface for viewing the measurements, analyzing the measurements (for example, generating a plot of the measurements versus one or more parameters), and, in some embodiments, transmitting the measurements to another computer, such as via a wireless network. The portable computer 412 may be similar to the portable computer 212 described above and may include similar components.

Figure 5:
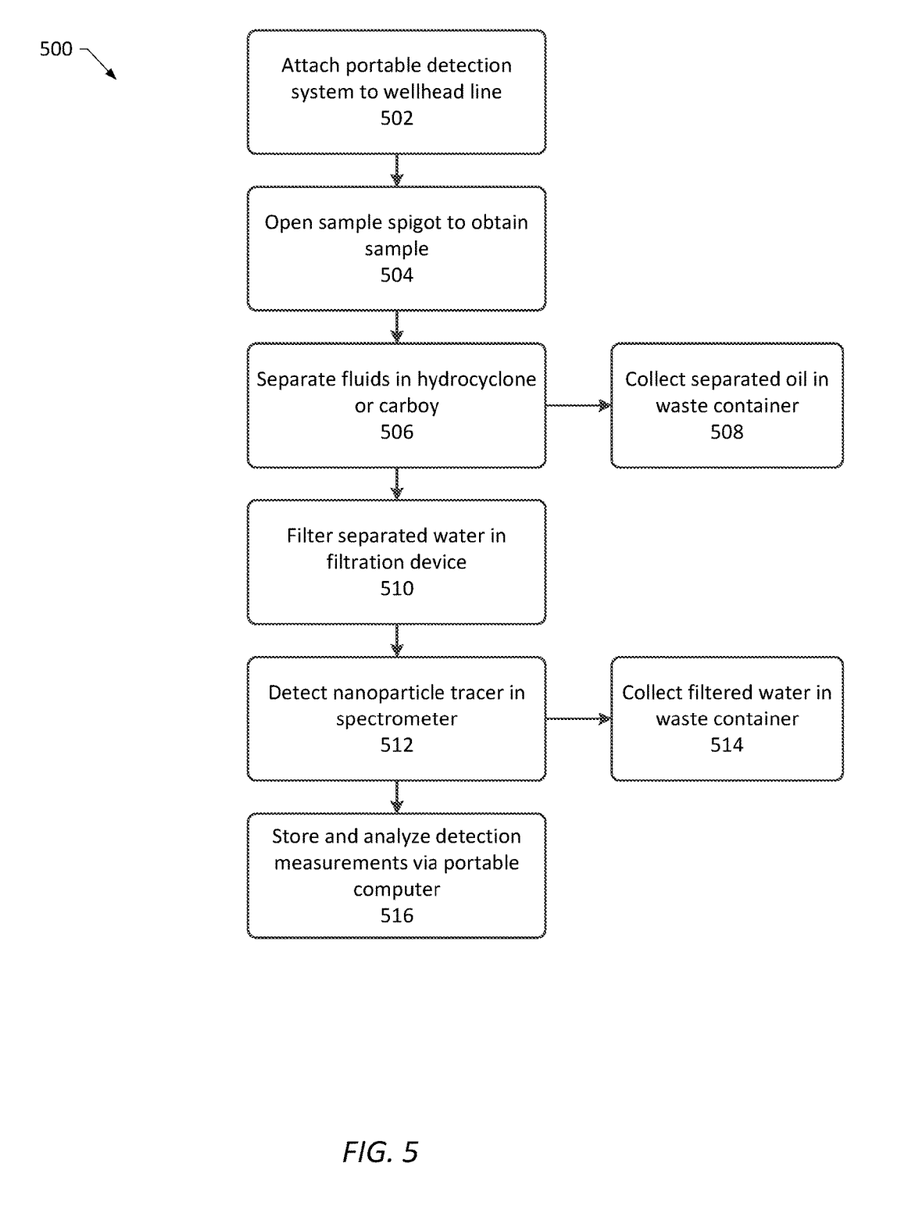
FIG. 5 is a block diagram of a process of the operation of a portable sensing system in accordance with an embodiment of the disclosure.

FIG. 5 depicts a process 500 for operation of a portable sensing system in accordance with an embodiment of the disclosure. As will be appreciated, one or more nanomaterial tracers may be introduced into a reservoir through an injector well, where they flow through the reservoir and to a producing well in fluid communication with the injector well. Thus, the process 500 may be used to analyze a producing well after introduction of the nanomaterial tracers. For example, the producing well may be analyzed to determine the suitable of intervention activities, such as rectifying unfavorable oil sweep and recovery conditions existing in a reservoir, plugging super-permeable zones for enhanced conformance during waterfloods, or for delivering chemicals to targets deep within a reservoir to alter wettability, reduce interfacial tensions, and/or enhance oil recovery.

Initially, the portable sensing system may be connected to a spigot in a sample line or producing line of a wellhead (block 502). In other embodiments, the portable sensing system may be connected to any suitable line or connector that enables a sampling of fluid from the wellhead. As noted herein, the portable sensing system may be connected to the wellhead without requiring modification of the wellhead and using existing components of the wellhead. For example, the portable sending system may be connected to a spigot of a wellhead line (for example, a producing line) using hose, pipe, or other tubing.

The spigot of the sample line or producing line may be opened to obtain a sample of production fluid (block 504). In some embodiments, the spigot may be opened manually by an operator to obtain a sample. In such embodiments, the spigot may be opened periodically to obtain period samples of production fluid from the wellhead. For example, samples may be obtained daily, weekly, multiple times a week, monthly, or other suitable periods. As will be appreciated, the production fluid obtained via the open spigot may be pressurized. Thus, in some embodiments, samples may be obtained without an automatic sample and without pumps or any electrically powered devices.

Next, fluids in the sample may be separated in a hydrocyclone or a carboy of the portable sensing system (block 506). The separation may occur via gravity, without any moving parts, and without the use of pumps or other electrically powered components. For example, as explained above, higher density fluid (for example, water) in the sample may be separated from lower density fluid (for example, oil) in the sample. In some embodiments, the separated oil may be collected in a waste container (block 508). For example, separated oil may be directed from the top of a hydrocyclone to the waste container, or the separated oil may be periodically emptied from a carboy.

The separated water from the one or more hydrocyclones or the carboy may be filtered in a filtration device (block 510). As discussed above, the filtration device may include suitable filtration media for separating contaminants that may interfere with detection of the fluorescent nanomaterial tracers in the separated water and that does not modify the signature of the nanomaterial tracers, and also has a suitable service life. The filtration may occur via gravity, fluid pressure, or both, without any moving parts, and without the use of pumps or other electrically powered components.

Next, the nanomaterial tracer in the filter water may be detected by a spectrometer (block 512). In some embodiments, the spectrometer may be powered solely by power received from a portable computer, by a battery directly coupled to or in a housing of the spectrometer, or by a combination of a battery and power received from the portable computer. In some embodiments, the filtered water used in the spectrometer may also be collected in the waste container (block 514).

The detection measurements from the spectrometer may be provided to a portable computer for storage and analysis (block 516). For example, as described above, in some embodiments the portable computer may display the measurements received from the portable spectrometer, such as in a table or as a graph (for example, a graph of intensity vs. wavelength). In some embodiments, the portable computer may transmit the detection measurements to a remote computer, such as over a network (for example, a cellular network).

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A portable system for detecting nanomaterial tracers in fluid produced from a well, comprising:
   a separation device connectable to a wellhead without modification of the wellhead, the separation device configured to receive a sample of production fluid from the wellhead and separate crude oil and water in the sample, wherein the separation device comprises a hydrocyclone or a carboy operable without electric power;
   a filtration device connected to the separation device and comprising filtration media, wherein the filtration device is operable without electric power to filter a separated fluid received from the separation device; and
   a spectrometer connected to the filtration device and operable to receive a filtered fluid from the filtration device and measure a spectrum of the filtered fluid.

2. The portable system of claim 1, comprising a portable computer coupled to the spectrometer via a wired connection.

3. The portable system of claim 2, wherein the spectrometer is operable to receive power solely from the portable computer via the wired connection.

4. The portable system of claim 1, comprising a waste container arranged to receive crude oil from the filtration device.

5. The portable system of claim 4, wherein the waste container is further arranged to receive the filtered fluid from the spectrometer after measurement of the spectrum.

6. The portable system of claim 1, wherein the filtration media comprises a clay comprising zeolite.

7. The portable system of claim 1, wherein the spectrometer comprises a light-emitting diode (LED) or a laser diode array arranged to emit light into a test cell, the test cell configured to contain the filtered fluid.

8. The portable system of claim 1, wherein the sample comprises a nanoparticle tracer, such that the spectrum indicates fluorescence emitted by the nanoparticle tracer at a wavelength.

9. The portable system of claim 1, wherein the wellhead comprises a line comprising a spigot, wherein the separation device is configured to be connected to the spigot.

10. The portable system of claim 1, wherein the system does not include a pump.

11. A method for detecting nanomaterial tracers in fluid produced from a well, comprising:
    receiving a sample of a production fluid from a wellhead in a separation device configured to separate crude oil and water in the sample, wherein the separation device comprises a hydrocyclone or a carboy operable without electric power, where the separation device is connected to the wellhead without modification of the wellhead;
    separating, by the separation device, the crude oil and the water in the sample;
    filtering, by a filtration device connected to the separation device, the separated water, wherein the filtration device comprises filtration media; and
    measuring, via a spectrometer connected to the filtration device, a spectrum of the filtered water.

12. The method of claim 11, comprising transmitting the measurements over a wired connection from the spectrometer to a portable computer.

13. The method of claim 12, wherein the spectrometer is operable to receive power solely from the portable computer via the wired connection.

14. The method of claim 11, comprising disposing the separated crude oil in a waste container connected to the separation device.

15. The method of claim 11, wherein the filtration media comprises a clay comprising zeolite.

16. The method of claim 11, wherein the spectrometer comprises a light-emitting diode (LED) or a laser diode array arranged to emit light into a test cell, the test cell configured to contain the filtered fluid.

17. The method of claim 11, wherein the sample comprises a nanoparticle tracer, such that the spectrum indicates fluorescence emitted by the nanoparticle tracer at a wavelength.

18. The method of claim 11, wherein the wellhead comprises a line comprising a spigot, the method comprising connecting the separation device to the spigot.

\* \* \* \* \*